(12) United States Patent
Elam et al.

(10) Patent No.: US 7,511,938 B2
(45) Date of Patent: Mar. 31, 2009

(54) FILTERING ASSEMBLY AND A FEEDTHROUGH ASSEMBLY

(75) Inventors: Ralph Elam, Beaverton, OR (US); Philip J. Atkin, West Linn, OR (US); Michael J. Ayton, Beaverton, OR (US); Marion Ronald LeCompte, Portland, OR (US); Dennis Digby, Wilsonville, OR (US); Habib Homayoun, Beaverton, OR (US)

(73) Assignee: Biotronik CRM Patent AG, Baar (CH)

( * ) Notice: Subject to any disclaimer, the term of this patent is extended or adjusted under 35 U.S.C. 154(b) by 0 days.

(21) Appl. No.: 12/060,227

(22) Filed: Mar. 31, 2008

(65) Prior Publication Data
US 2008/0247117 A1  Oct. 9, 2008

Related U.S. Application Data

(60) Provisional application No. 60/909,722, filed on Apr. 3, 2007.

(51) Int. Cl.
*H01G 4/35* (2006.01)
(52) U.S. Cl. .................. 361/302; 361/303; 361/305; 361/307; 607/5; 607/9; 607/36; 607/37
(58) Field of Classification Search ................ 361/302, 361/303–305, 307; 607/5, 9, 36–37
See application file for complete search history.

(56) References Cited

U.S. PATENT DOCUMENTS

| 5,650,759 | A | 7/1997 | Hittman et al. |
| 5,896,267 | A | 4/1999 | Hittman et al. |
| 5,999,398 | A * | 12/1999 | Makl et al. .................. 361/302 |
| 6,459,935 | B1 | 10/2002 | Piersma |
| 6,822,248 | B2 | 11/2004 | Ferrera et al. |
| 6,963,780 | B2 * | 11/2005 | Ruben et al. .................. 607/36 |
| 6,987,660 | B2 | 1/2006 | Stevenson et al. |
| 7,310,216 | B2 * | 12/2007 | Stevenson et al. ........... 361/302 |
| 7,391,601 | B1 * | 6/2008 | Imani ......................... 361/302 |

* cited by examiner

*Primary Examiner*—Nguyen T Ha
(74) *Attorney, Agent, or Firm*—Dalina Law Group, P.C.

(57) ABSTRACT

Filtering assembly for a feedthrough, for implantable medical devices, having operating conductive pin(s) and a ground conductive pin. The filtering assembly has:
 first insulating substrate,
 first conductive layer accommodated at first side of first insulating substrate and second conductive layer accommodated at second side of first insulating substrate opposing first side,
 first conductive layer comprises a conductive ground ring accommodated that surrounds the circumference of one end of the operating conductive pins and capacitive element(s), wherein each of the capacitive element(s) provides on the first side a connection to the operating conductive pin(s) and on the second side a connection to the ground ring, wherein the ground ring is connected to the ground pin,
 the second conductive layer comprises a ground plane providing connection to the ground ring of the first conductive layer and a connection to the ground pin.

Further directed to a feedthrough assembly comprising the inventive filtering assembly.

11 Claims, 5 Drawing Sheets

FILTERING ASSEMBLY AND A FEEDTHROUGH ASSEMBLY

This application claims the benefit of U.S. Patent Application 60/909,722, filed 3 Apr. 2007, the specification of which is hereby incorporated herein by reference.

BACKGROUND OF THE INVENTION

1. Field of the Invention

The present invention relates to a filtering assembly for a feedthrough, preferably for implantable medical devices, wherein said feedthrough comprises at least one operating conductive pin and a ground conductive pin and a respective feedthrough assembly.

2. Description of the Related Art

Feedthrough assemblies are generally well-known in the art for connecting electrical signals through the housing or case of an electronic instrument, for example of an active implantable medical device, such as a cardiac pacemaker, an implantable hearing device, a defibrillator, a neurostimulator, a drug pump or the like.

A known feedthrough assembly comprising a multitude of electrically conductive pins is disposed within a respective one of a multitude of openings in an insulator structure for feedthrough passage from the exterior to the interior of the electronic instrument. The end of each cylindrically formed pin of the multitude of electrically conductive pins protruding to the exterior of the electronic device is referred to as the first end of each pin and the opposite end of the each pin is referred to as the second end. The second end of the pin is electrically connected to an interior element of the electronic instrument transferring or receiving the electrical signals. The known feedthrough assembly further comprises an insulating element (in the following: header) having a supportive surface with a flange and/or a recess on the outer perimeter thereof. This supportive surface serves as a leakproof attachment of the feedthrough assembly to the housing.

Today it is often requested with regard to active implantable medical devices to decouple and/or shield undesirable electromagnetic interference signals (EMI signals) from the device wherein electromagnetic interference signals consist of a number of modulated carrier frequencies, for example the carrier frequency of a cellular phone.

In order to filter (decouple and/or shield) these undesirable electromagnetic interference signals it is well-known in the art that EMI feedthrough capacitors can be attached to the flanges of human implantable seals. These devices are generally designed with one or more monolithic ceramic feedthrough capacitors which are typically made of a barium titanate dielectric into which alternating active and ground electrode plates are embedded.

In U.S. Pat. No. 6,822,248 B2 an EMI filtered connector is disclosed which provides a multitude of conductive terminal pins, a grounded conductive connector housing through which the terminal pins pass in a non-conductive relation, and an array of feedthrough filter capacitors each having a distinct first set of electrode plates (refers to a set of electrode plates which are distinctly separate and associated with a particular capacitor of the feedthrough filter capacitor array), a non-distinct second set of electrode plates (refers to those plates which are common to two or more of the distinct capacitors in the array of feedthrough filter capacitors) and first passage way through which a respective terminal pin extends in conductive relation with the first set of electrode plates. Further, at least one ground lead conductively coupled to the conductive connector housing and extending into a second passage way through the array of feedthrough filter capacitors in conductive relation with the second set of electrode plates and a grounding ring conductively coupled to the ground lead and to the connector housing are provided.

Document U.S. Pat. No. 6,987,660 B2 describes feedthrough capacitors which are typically formed of a dielectric material having disposed therein in an alternating fashion ground electroplates and active electroplates. A passage way is provided through the capacitor which is lined with a metallization layer typically applied either by a thick film process or by selective electroplating. Additionally, metallization is applied about the periphery of the capacitor in a similar manner as the interior metallization. The exterior metallization provides the electrical contact to the ground electrode plate set. For conductively coupling the terminal pin and the first set of electrodes and for mechanically coupling the terminal pin to the feedthrough capacitor the feedthrough terminal assembly described in this document comprises a terminal pin which at least partially extends through the aperture. A conductive insert is disposed within the aperture. In one embodiment, the insert further comprises a resiliently flexible conductive contact spring which provides the electrical contact between the inside diameter of the feedthrough hole of the ceramic capacitor and the lead wire of a terminal pin.

The above mentioned state of the art feedthrough assemblies for EMI filtering have the disadvantage, that on the one hand they are expensive in manufacturing and on the other hand it is impossible to get reliable results in leakage testing because of their complicated structure. Additionally, the state of the art feedthrough assemblies can not easily be minimized.

In U.S. Pat. No. 6,459,935 B1 a filtered feedthrough assembly is disclosed comprising a header having a supportive surface and a discoidal capacitive device with an upper and a lower side, wherein the lower side is connected or bonded to the supportive surface of the header. The discoidal capacitive device comprises a first set of electrode plates arranged to be suitable for parallel connections with the multiple electrically conductive terminal pins, a second set of electrode plates arranged to be suitable for series connections with the multiple electrically conductive terminal pins and a second set of openings defined through said discoidal capacitive device for the passage of the terminal pins, wherein electrically conductive patterns are disposed on said upper side of said discoidal capacitor and an electrical component is connected to said electrically conductive patterns. The discoidal capacitor is bonded to the supportive surface of the header with a conductive polyamide. This feedthrough assembly can be manufactured more easily and less expensively than the feedthrough assemblies above mentioned and allows for the integration of additional electronic components into the assembly. However, the direct connection or bonding of the discoidal capacitive device to the supportive surface of the header may cause difficulties in the manufacturing procedure and result in less reliability during its operation because the header and the discoidal capacitive device have different thermal expansion coefficient.

Therefore it is desirable to provide a multi-leaded feedthrough assembly and a filtering assembly therefore capable of reliably filtering EMI at the point of entry of the signals into the implantable medical device and which can be manufactured easily and inexpensively, tested with reliable results and allows for integration of further electrical components.

BRIEF SUMMARY OF THE INVENTION

According to the present invention a filtering assembly is provided which comprises the following elements:
- a first insulating substrate;
- a first conductive layer accommodated at a first side (at the top side) of said first insulating substrate and a second conductive layer accommodated at a second side (at the bottom side) of said first insulating substrate opposing said first side;
- said first conductive layer comprises a conductive ground ring accommodated in the way that it surrounds the circumference of one end of said operating conductive pins and at least one capacitive element, wherein each of said at least one capacitive elements provides on the first side a connection to one or more of said operating conductive pins and on the second side a connection to said ground ring, wherein said ground ring is connected to said ground pin;
- said second conductive layer comprises a ground plane providing a connection to said ground ring of said first conductive layer and a connection to said ground pin.

The inventive filtering assembly provides effective EMI filtering for feedthroughs, in particular for implantable medical devices. It suppresses EMI energy from influencing the performance of the device. The (integrated) inventive filtering assembly consists of a two conductive layer (preferably metal layer) substrate and preferably ceramic filter capacitors as capacitive elements. The top side conductive layer is patterned to shunt the EMI energy via the capacitive element(s) to a ground ring which surrounds the circumference of the feedthrough points. The bottom side conductive layer provides a ground plane which encompasses the area under the capacitive element(s) and extends to the top side ground ring. This ground plane is used to shunt any radiated EMI energy. Both the top side ground ring and the bottom side ground plane are connected to the ground pin of the feedthrough, thus shunting the EMI energy to the case of the device. The ground plane of the second conductive layer acts as a faraday cage thus shielding EMI from entering the device and disrupting the operation of the device, for example the pacemaker. The ground ring of the first conductive layer provides EMI shielding as well as a low resistance and a low inductive path. Therein the ground ring realizes low physical size so as to cope with the manufacturing limits.

In a preferred embodiment the filtering assembly comprises four capacitive elements at the first conductive layer, wherein each of said four capacitive elements provides a connection to one of said four operating pins of said feedthrough. This embodiment realizes the filtering assembly in the case that the feedthrough comprises four operating pins.

In a further preferred embodiment the filtering assembly comprises at least one capacitive element which is formed by a ceramic capacitor. Ceramic capacitors are very reliable in operation and have a low thermal coefficient.

In a further preferred embodiment the filtering assembly comprises first and said second conductive layers which are formed by metal layers.

Further, according to the present invention a feedthrough assembly is provided, preferably for implantable medical devices, which comprises at least one operating conductive pin and a ground conductive pin and a filtering assembly described above, wherein said ground ring and said ground plane is connected to said ground pin and each of said at least one capacitive elements is connected to one or more of said operating pins.

The inventive feedthrough assembly has excellent EMI filtering properties and is easy to manufacture at low cost.

In a preferred embodiment the feedthrough assembly comprises:
- a header having a supportive surface with a flange and/or a recess on the outer perimeter thereof for attachment to a housing dividing the header in an outer section and an inner section;
- a second insulating substrate which is accommodated close to the inner section of the header;
- said filtering assembly which is either directly attached to, preferably with its second conductive layer, or embedded within said second insulating substrate;
- said operating pins each having respective first and a second ends and each being disposed within a respective one of a multitude of openings in the header, in the second insulating substrate and, if applicable, in the filtering assembly lying upon each other, wherein the second ends of the conductive pins are electrically connected to one of said capacitive elements of said first conductive layer of said filtering assembly.

The inventive multi-leaded feedthrough assembly is capable of reliably filtering EMI at the point of entry of the signals into the implantable medical device. The assembly can be manufactured easily and inexpensively, tested with reliable results and allows for integration of further electrical components.

In a preferred embodiment, the insulating substrate is a flexible arm.

In a further preferred embodiment the insulating substrate is formed as a tape having a first and a second end and which is bent as a loop, wherein said filtering assembly is attached to or embedded within the first end of the tape and the second end of the tape is attached to an interior element of said implantable device contained within the housing electrically connecting the wiring pattern to a connector of the interior element. Preferably, the insulating substrate is bent as a loop so that the first end and the second end of the tape are at least almost touching one another. Thereby, the first end of the tape is supported by the second end of the tape and is not freely moving within the housing.

In a further preferred embodiment the at least one operating pin and said ground pin of the inventive filtering feedthrough assembly is attached to the header by means of a glass solder. The glass solder serves as leakage proof closure of the gap between the conducting pin and the header. Additionally, the filtering assembly is mounted in the way that it does not interfere with the leek proof aspect of the feedthrough assembly.

Additionally the first conductive layer is accommodated at the side of the second insulating substrate that is not directed to the inner section of the header but at the side of the second insulating substrate that is directed to the opposite direction. Thereby any mechanical contact between the first conductive layer and the header can be avoided leading to a longer working life of the filtering assembly.

Preferably, the filtering assembly comprises a capacitor array connected on one side with each of its leads to one of the multitude of electrically conducting operating pins and on the other side to ground or the filtering assembly comprises at least two parallel capacitors wherein each capacitor is connected on one side to one of said multitude of operating pins and on the other side to ground. Preferably, the capacitors can be combined with inductors forming low pass or high pass filters. In a more preferred embodiment the filtering assembly comprises four capacitors with equal capacitance.

In another embodiment there is a clearance between the end face of the inner section of the header opposite to the second insulating substrate and the second insulating substrate. This clearance can be advantageous especially with regard to defibrillators because leakage/creepage currents are avoided.

BRIEF DESCRIPTION OF THE DRAWINGS

A full and enabling disclosure of the present invention, including the best mode thereof, directed to one of ordinary skill in the art, is set forth in the following specification of different embodiments. Thereby, further features and advantages are presented that are part of the present invention independently of the appended claims. The specification makes reference to the accompanying figures, in which:

DETAILED DESCRIPTION OF THE INVENTION

Figure 1:
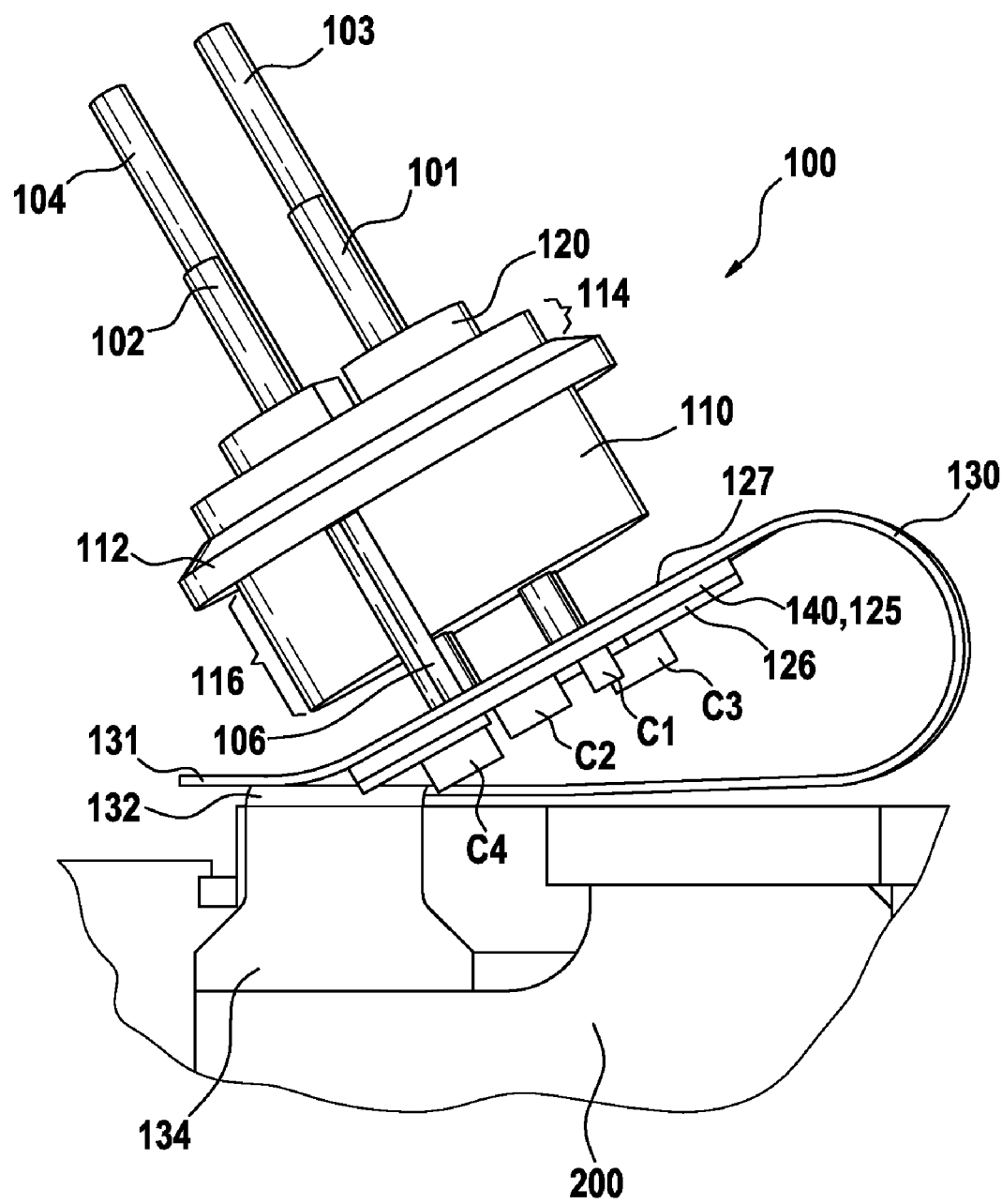
FIG. 1 is a schematic perspective side view of an exemplary embodiment of the present invention illustrating an inventive feedthrough assembly connected to an interior element.

FIG. 1 depicts a preferred embodiment of an inventive feedthrough assembly 100 which is connected to an interior element 200 of an implantable medical device, such as a cardiac pacemaker. The interior element 200 may transfer or process the electrical signals which are connected through the housing or case (not shown) of the medical device.

The feedthrough assembly 100 comprises four cylindrically conducting pins 101, 102, 103 and 104 (operating pins). The pins 101 and 102 protrude with shorter ends from the upper side (in FIG. 1) of a header 110 compared to the length of the protruding ends of pins 103 and 104, respectively. These ends of pins 101 to 104 are referred to as first ends. The assembly 100 further comprises a cylindrically ground pin 106. The pins 101 to 104 and 106 are preferably made of a metal.

The operating pins 101 to 104 and ground pin 106 are disposed within respective openings in the cylindrically formed header 110, wherein the pins 101 to 104 fully pass the header 110 and protrude on the lower side of the header 110. The ground pin 106 also protrudes from header 110 on its lower side but not from its upper side. The ends of the operating pins 101 to 104 and ground pin 106 protruding on the lower side of the header 110 are referred to as the second end of each pin. The opening of ground pin 106 is accommodated within the flange 112 of the header which is used to fix the header within an opening of the housing or case (not shown) of the implantable device. The upper section of the header 110 from the upper end surface of the header 110 to the flange 112 is referred to as outer section 114 and the remaining section from the flange 112 to the lower end surface of the header 110 is referred to as inner section 116, as the inner section 116 of the header is situated within the housing and the outer section 114 is not situated within the housing of the implantable device if the header 110 is placed within the respective opening of the housing.

The openings of the operating pins 101 to 104 are hermetically and leak-proof closed by a glass solder 120. The glass solder 120 extends to the end surface of the outer section 114 of the header 110 and covers this surface at least partially.

The inventive feedthrough assembly 100 further comprises an inventive filtering assembly (feedthrough daughter board) 140 which comprises a first insulating substrate 125 imprinted on the first (top) side by a first (top) conductive layer 126 and on the second opposite (bottom) side by a second (bottom) conductive layer 127. The feedthrough assembly further comprises a second insulating substrate 130 comprising an electrical signal path formed in this example like a tape which is bent in a loop forming a flexible arm that runs between the inventive filtering assembly 140 and the interior element 200 of an implantable medical device such as a cardiac pacemaker.

The second insulating substrate 130 is accommodated underneath the header 110 close to the end face of the inner section 116 of the header 110. The tape comprises a first end 131 and a second end 132, wherein the first end 131 and the second end are positioned on top of one another and are almost touching one another. Thereby, the first end 131 is accommodated close to the end face of the inner section 116 of the header 110. The end section of the first end 131 of the second insulating substrate 130 is a little, approximately by an angle of 30°, bent off from the remaining part of the first end 131 of the second insulating substrate 130 to which the inventive filtering assembly 140 is attached. The second end 132 of the second insulating substrate 130 runs parallel to the surface of the interior element 200 of the medical device to which the second insulating substrate 130 is attached.

The filtering assembly (circuit board) 140 is attached with its second conductive layer 127 to that side of the first end 131 of the second insulating substrate 130 which points away from the header 110. The circuit board 140 is soldered or attached using an adhesive to the second insulating substrate 130.

The second end 132 of the insulating substrate comprises a section 134 which is accommodated sideways with regard to the lateral dimension of the tape-like second insulating substrate 130. The section 134 provides a mechanical connection of the second insulating substrate 130 of the feedthrough assembly 100 to the interior element 200 of the implantable medical device by means of its claw-like form.

The second insulating substrate 130 (flex arm bridge) contains conductor paths (signal paths, not shown) leading from connections (not shown) to the operating pins 101 to 104 and to ground pin 106 (where required) at the first end 131 to the second end 132 of the second insulating substrate 130 leading the feed-through signals to the interior element 200 of the medical device which is electrically connected to the conductor paths and thereby to operating pins 101 to 104 and to ground pin 106 (where required).

Figure 2:
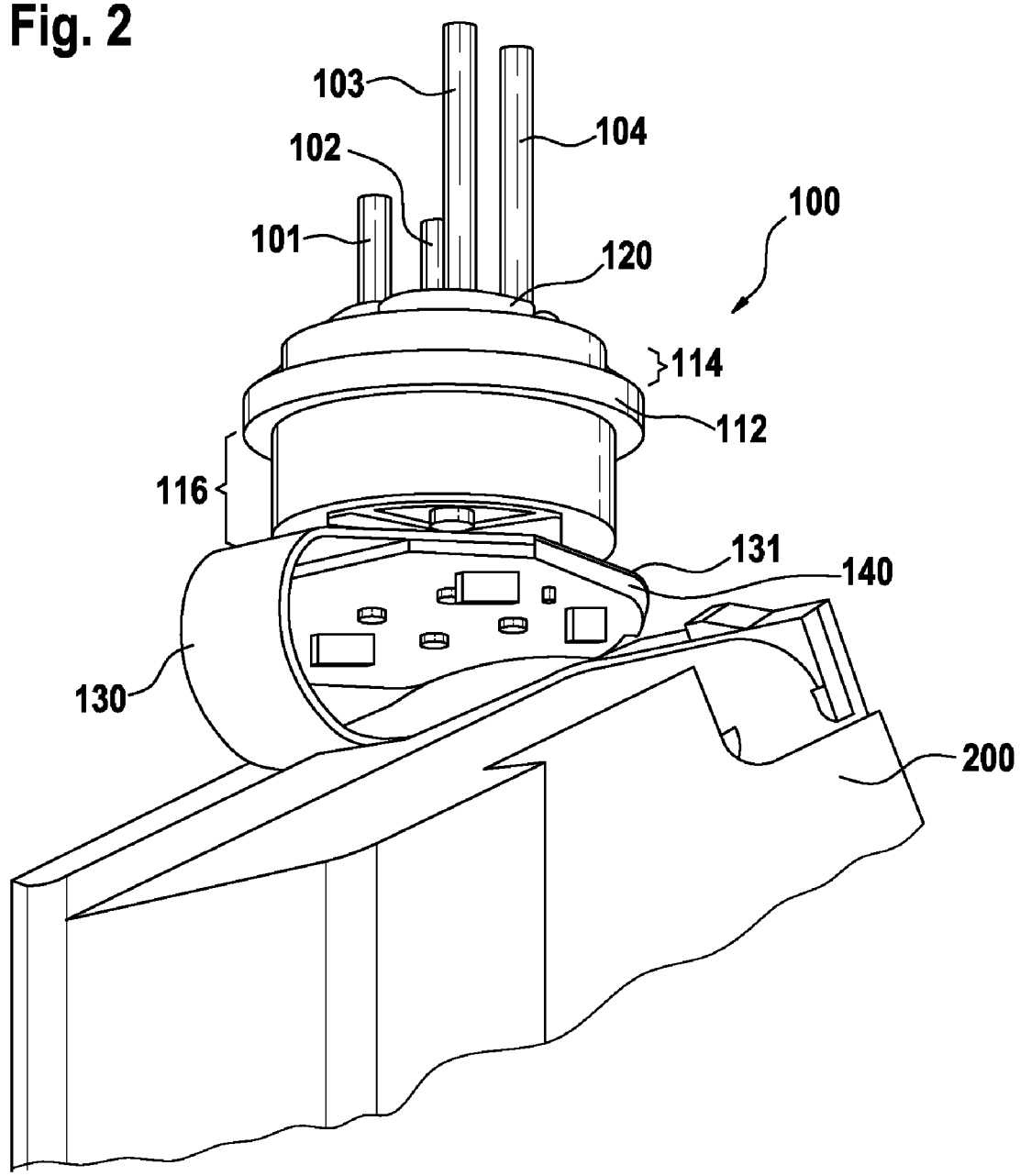
FIG. 2 is another schematic perspective view of the exemplary embodiment of FIG. 1.
Figure 3:
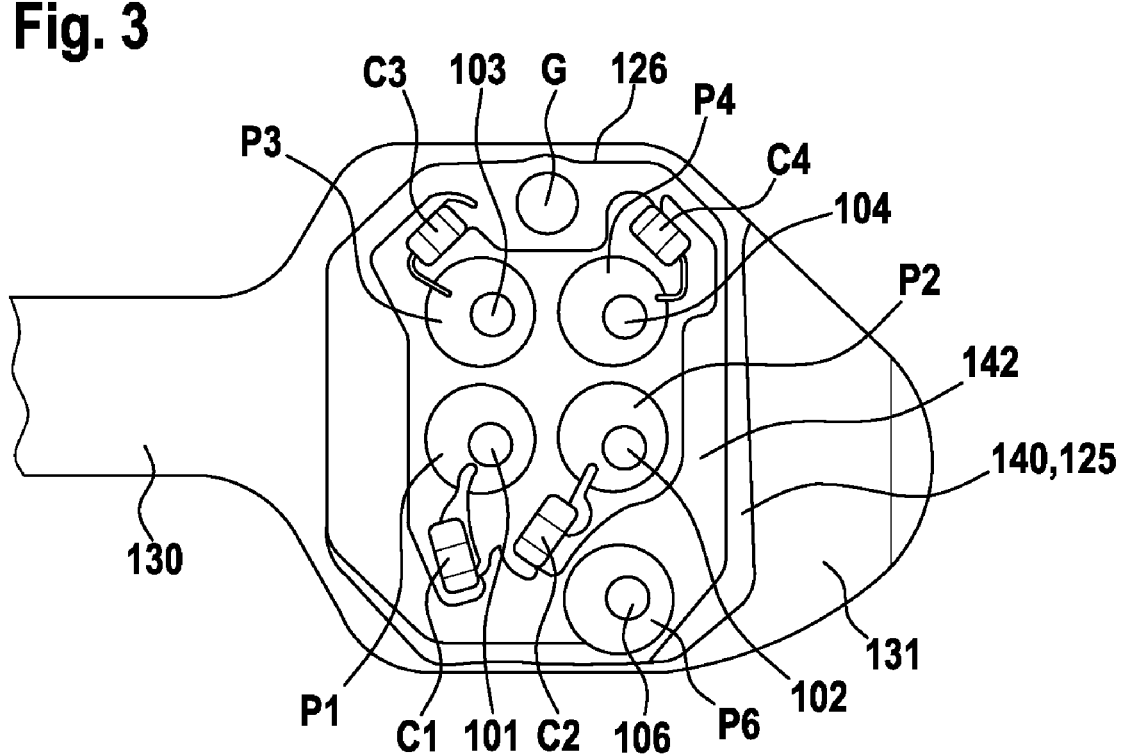
FIG. 3 shows a photographic top view of the top side of the inventive filtering assembly of the inventive feedthrough assembly of FIG. 1, wherein the filtering assembly is attached to the first end of the second insulating substrate.

The insulating substrate 125 of the inventive filtering assembly 140 is formed as a polygonal plate. A first conductive layer 126 forming a wiring pattern connected to at least one capacitive element is attached to the top side of the insulating substrate 125. An example of a first conductive layer 126 prepared to connect to four parallel capacitors C1, C2, C3, and C4 is shown in FIG. 3 by means of a photograph. In FIGS. 1 and 2 the filtering assembly 140 comprising four capacitors C1, C2, C3, and C4 are depicted as cuboids which are connected to the first conductive layer 126 by conventional surface mount technique.

Figure 4:
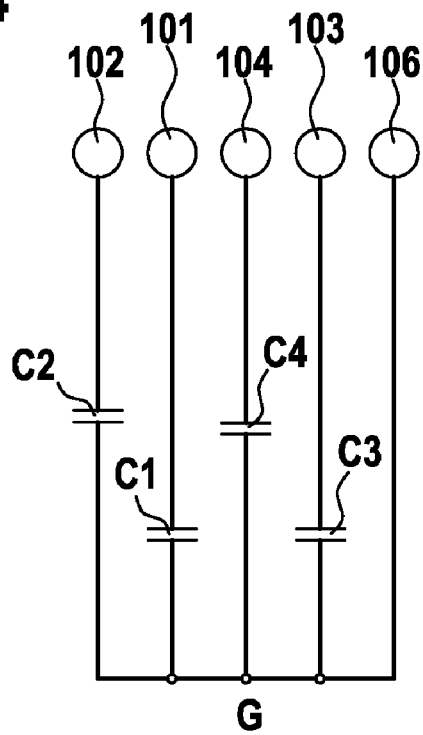
FIG. 4 depicts a wiring sketch of the conductive structure of the inventive filtering assembly shown in FIG. 3.

As best seen in FIG. 3 the second ends of the operating pins 101 to 104 and of the ground pin 106 are connected by means of conducting pads (through hole solder joint) to the wiring pattern (first conductive layer 126) of the circuit board 140. The pads are provided with the reference numbers P1, P2, P3, and P4 of operating pins 101, 102, 103, and 104, respectively, and with reference number P6 of ground pin 106. The pads P1, P2, P3, and P4 of pins 101, 102, 103, and 104 are connected in parallel with a capacitor C1, C2, C3, C4, respectively. Each capacitor C1 to C4 is on the other side (side opposite to the electrical connection to one of the pads P1 to P4) electrically connected to ground G. The ground pin 106 is connected via pad P6 to ground G. The respective wiring diagram of this example is shown in FIG. 4.

Figure 5:
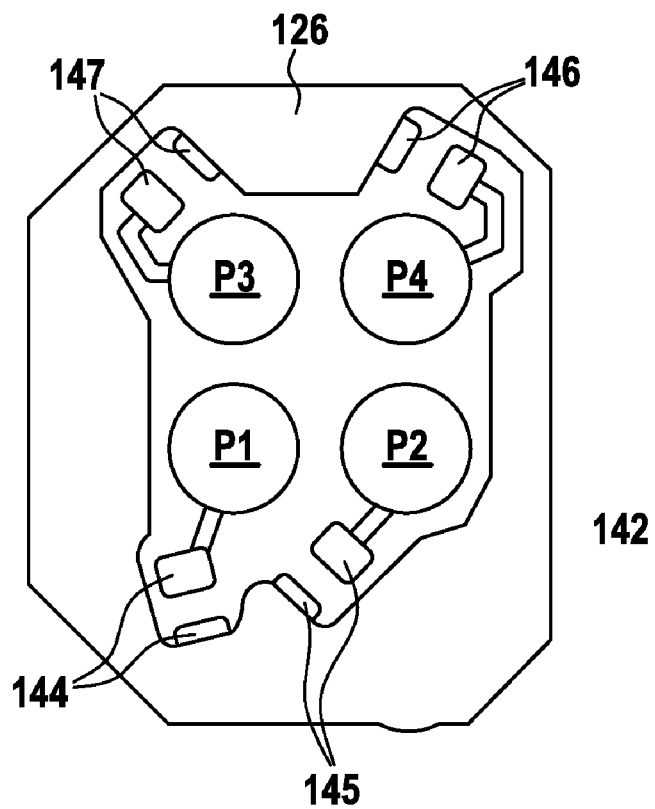
FIG. 5 shows a schematic top view of the first conductive layer (top conductive layer) of the inventive filtering assembly used in the feedthrough assembly of FIGS. 1 to 3 made for four parallel capacitors as capacitive elements, wherein the first conductive layer is directly imprinted to the first insulating substrate of the inventive filtering assembly.
Figure 6:
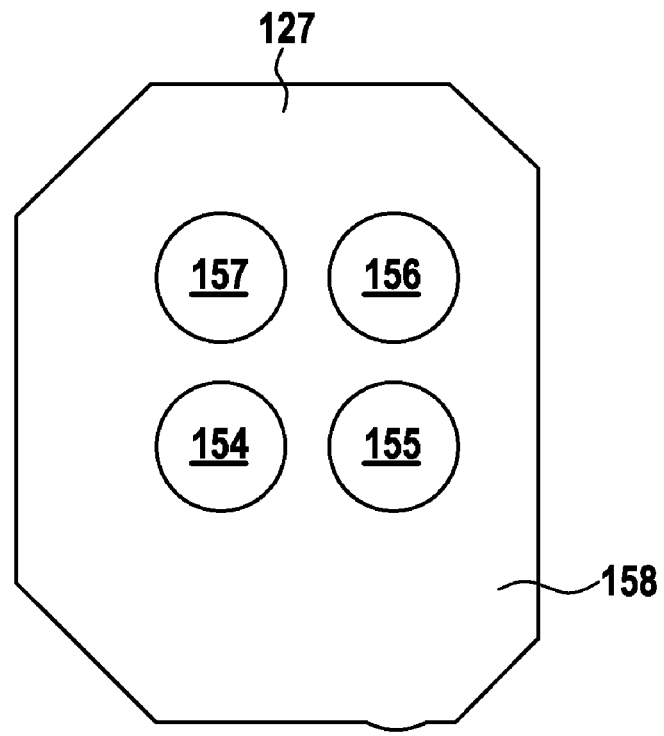
FIG. 6 shows a schematic top view of the second conductive layer (bottom conductive layer) of the inventive filtering assembly used in the feedthrough assembly of FIGS. 1 to 3, wherein the second conductive layer is directly imprinted to the first insulating substrate.

The conductive layers of the inventive filtering assembly are shown in FIGS. 5 and 6. The first conductive layer 126 is depicted in FIG. 5. The first conductive layer 126 is constructed for the connection to four operative pins with four pads P1, P2, P3, and P4 and a ground ring 142. The ground ring 142 surrounds the circumference of the feedthrough points (pads P1, P2, P3, and P4). It also comprises connections 144, 145, 146, and 147 for capacitors. The bottom conductive layer 127 is depicted in FIG. 6. It shows four pads 154, 155, 156, and 157 for connection with the operative pins 101, 102, 103, and 104 and a ground ring area 158 covering the entire outer surface of the bottom side of the first insulating substrate 125, encompassing the area under the capacitors C1, C2, C3, and C4 of the top side of the filtering assembly and extending to the ground ring 142 of the first conductive layer.

Figure 7:
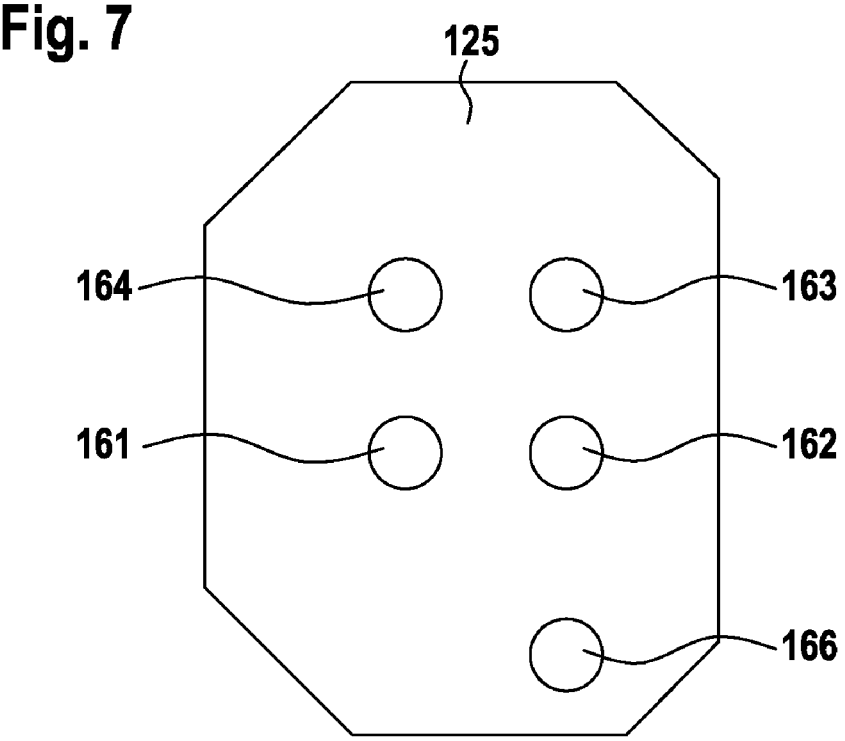
FIG. 7 depicts a schematic top view of the first insulating substrate of the inventive filtering assembly without the first conductive layer shown in FIG. 5 and without the second conductive layer shown in FIG. 6.

The insulating substrate 125 shown in FIG. 7 has a octagonal shape comprises five holes 161, 162, 163, and 164 which go through the insulating substrate 125 in order to hold the operative pins 101, 102, 103, and 104 and one through going hole 166 in order to hold the ground pin 106.

Figure 8:
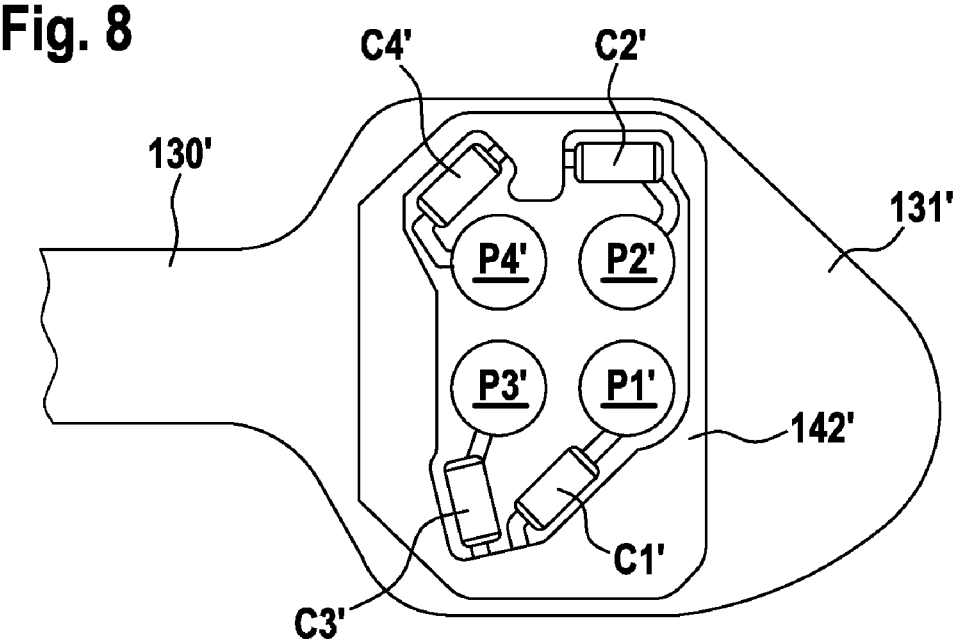
FIG. 8 shows a schematic top view of a further embodiment of the first conductive layer (top conductive layer) of an inventive filtering assembly made for four parallel capacitors as capacitive elements, wherein the first conductive layer is directly imprinted to the second insulating substrate of the feedthrough assembly.

Alternatively, the wiring pattern with pads P1' to P4' and ground G' with the filtering capacitors C1' to C4' can be incorporated directly on the first end 131' of the second insulating substrate 130', thus eliminating the need for a separate circuit board as a filtering assembly 140. This possibility is shown in FIG. 8. Therein, the first end 131' of the second insulating substrate 130' forms the insulating substrate of the filtering assembly. The first conductive layer 126' is imprinted directly to the first end 131' of the second insulating substrate 130'. The same is done with the second conductive layer (not shown) on the opposite side of the first end 131' of the second insulating substrate. The first conductive layer 126' of FIG. 8 comprises four pads P1', P2', P3', and P4' for the connection with the operating pins 101, 102, 103, and 104 and four capacitors C1', C2', C3', and C4'. The surrounding ground ring 142' is formed by two side bars and one lower bar and the right hand side bar, respectively. The upper part of the ground ring 142' is formed by ground G'.

The best mode of the invention is depicted in FIGS. 1, 2, 3, and 4 using four capacitors each of a capacity of 6800 pF (capacitor No. 40201). With the invention in its best mode a filtering feedthrough assembly is proposed which can be manufactured easily at significantly lower costs.

LIST OF REFERENCE NUMBERS 100 feedthrough assembly
101, 102 operating pin
103, 104 operating pin
106 ground pin
110 header
112 flange of the header
114 outer section of the header 110
116 inner section of the header 110
120 glass solder
125 first insulating substrate
126, 126' first conductive layer (top conductive layer)
127 second conductive layer (bottom conductive layer)
130, 130' second insulating substrate
131, 131' first end of the insulating substrate 130
132 second end of the insulating substrate 130
134 sideways section of the insulating substrate 130
140 filtering assembly (circuit board)
142, 142' ground ring
144 connection for capacitor
145 connection for capacitor
146 connection for capacitor
147 connection for capacitor
154, 155 pad for connection with operating pin 101, 102, respectively
156, 157 pad for connection with operating pin 103, 104, respectively
158 ground ring area
161, 162 through hole in substrate 125 for operating pin 101, 102, respectively
163, 164 through hole in substrate 125 for operating pin 103, 104, respectively
165 through hole in insulating substrate 125 for ground pin 106
200 interior element
C1, C1' capacitor
C2, C2' capacitor
C3, C3' capacitor
C4, C4' capacitor
P1, P1' pad of operating pin 101
P2, P2' pad of operating pin 102
P3, P3' pad of operating pin 103
P4, P4' pad of operating pin 104
P6, P6' pad of ground pin 106
G, G' ground

What is claimed is:

1. A filtering assembly for a feedthrough for implantable medical devices comprising:
   a feedthrough comprising
      at least one operating conductive pin and,
      a ground conductive pin;
   a filtering assembly comprising
      a first insulating substrate;

a first conductive layer accommodated at a first side of said first insulating substrate and a second conductive layer accommodated at a second side of said first insulating substrate opposing said first side;

said first conductive layer comprising a conductive ground ring accommodated in a way that surrounds a circumference of one end of said at least one operating conductive pin and at least one capacitive element, wherein each of said at least one capacitive element provides on a first side a connection to one or more of said at least one operating conductive pin and on a second side a connection to said conductive ground ring, wherein said conductive ground ring is connected to said ground conductive pin;

said second conductive layer comprising a ground plane that provides a connection to said conductive ground ring of said first conductive layer and a connection to said ground conductive pin.

2. The filtering assembly according to claim 1, wherein said first conductive layer comprises four capacitive elements, wherein each of said four capacitive elements provides a connection to one of said four operating pins of said feedthrough.

3. The filtering assembly according to claim 1 wherein said at least one capacitive element is formed by a ceramic capacitor.

4. The filtering assembly according to claim 1 wherein said first and said second conductive layers are formed by metal layers.

5. A feedthrough assembly for implantable medical devices, which comprises at least one operating conductive pin and a ground conductive pin and a filtering assembly according to claim 1, wherein said conductive ground ring and said ground plane are connected to said ground pin and each of said at least one capacitive element is connected to one or more of said at least one operating conductive pin.

6. The feedthrough assembly according to claim 5 comprising:

a header having a supportive surface with a flange and/or a recess on an outer perimeter thereof for attachment to a housing that divides the header into an outer section and an inner section;

a second insulating substrate which is accommodated close to the inner section of the header;

said filtering assembly which is either directly attached to, with its second conductive layer, or embedded within said second insulating substrate;

said at least one operating conductive pin each having respective first and a second ends and each being disposed within a respective one of a multitude of openings in the header, in the second insulating substrate and, if applicable, in the filtering assembly lying upon each other, wherein each of second ends of the at least one operating conductive pin is electrically connected to one of said at least one capacitive element of said first conductive layer of said filtering assembly.

7. The feedthrough assembly according to claim 6 wherein said second insulating substrate is a flexible arm.

8. The filtering feedthrough assembly according to claim 6 wherein said second insulating substrate is formed as a tape having a first end and a second end and which is bent as a loop, wherein said filtering assembly is attached to or embedded within said first end of said tape and the second end of said tape is attached to an interior element of said implantable device contained within said housing that electrically connects said filtering assembly to a connector of said interior element.

9. The filtering feedthrough assembly according to claim 7 wherein said second insulating substrate is bent as a loop so that said first end and said second end of said tape are at least almost touching one another.

10. The filtering feedthrough assembly according to claim 5, wherein said at least one operating conductive pin and said ground conductive pin are attached to said header by a glass solder.

11. The filtering feedthrough assembly according to claim 6, wherein there is a clearance between an end face of said inner section of said header opposite to said second insulating substrate and said second insulating substrate.

* * * * *